United States Patent
Yampolsky et al.

(10) Patent No.: US 7,628,806 B2
(45) Date of Patent: Dec. 8, 2009

(54) STENT WITH IMPROVED RESISTANCE TO MIGRATION

(75) Inventors: Ilya Yampolsky, W. Roxbary, MA (US); John Spiridigliozzi, Sharon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 506 days.

(21) Appl. No.: 10/643,261

(22) Filed: Aug. 20, 2003

(65) Prior Publication Data

US 2005/0043784 A1 Feb. 24, 2005

(51) Int. Cl.
*A61F 2/06* (2006.01)
(52) U.S. Cl. ...................................... 623/1.35
(58) Field of Classification Search ............... 623/1.15, 623/1.2, 1.35; 606/191–198
See application file for complete search history.

(56) References Cited

U.S. PATENT DOCUMENTS

| | | | |
|---|---|---|---|
| 4,655,771 A | 4/1987 | Wallsten | 623/1 |
| 4,944,071 A | 7/1990 | Marzoli | 19/80 |
| 5,061,275 A | 10/1991 | Wallsten | 623/1 |
| 5,226,913 A | 7/1993 | Pinchuk | 623/1 |
| 5,383,892 A | 1/1995 | Cardon | 606/198 |
| 5,395,390 A | 3/1995 | Simon | 606/198 |
| 5,639,278 A | 6/1997 | Dereume et al. | 623/1 |
| 5,693,086 A | 12/1997 | Gorcoechea | 623/1 |
| 5,723,004 A | 3/1998 | Dereume | 623/1 |
| 5,755,735 A | 5/1998 | Richter | 606/194 |
| 5,836,966 A | 11/1998 | St. Germain | 606/198 |
| 5,843,160 A | 12/1998 | Rhodes | 623/1 |
| 5,855,598 A | 1/1999 | Pinchuk | 623/1 |
| 5,906,640 A | 5/1999 | Penn | 623/1 |
| 6,017,363 A | 1/2000 | Hojeibane | 623/1 |
| 6,068,655 A | 5/2000 | Sequin | 623/1 |
| 6,102,938 A | 8/2000 | Evans | 623/1 |
| 6,146,403 A | 11/2000 | St. Germain | 606/198 |
| 6,168,621 B1 | 1/2001 | Vrba | 623/1.2 |
| 6,273,909 B1 | 8/2001 | Kugler | 623/1.13 |
| 6,273,910 B1 | 8/2001 | Limon | 623/1.13 |
| 6,325,819 B1 * | 12/2001 | Pavcnik et al. | 623/1.11 |
| 6,387,120 B2 | 5/2002 | Wilson | 623/1.11 |
| 6,423,084 B1 | 7/2002 | Germain | 606/198 |

(Continued)

FOREIGN PATENT DOCUMENTS

EP 0 800 801 10/1997

(Continued)

OTHER PUBLICATIONS

Communication Pursuant to Article 96(2) EPC, for application 04 780 261.6-2310, dated Oct. 19, 2007.

(Continued)

*Primary Examiner*—Kevin T Truong
(74) *Attorney, Agent, or Firm*—Brooks, Cameron & Huebsch, PLLC

(57) ABSTRACT

A bifurcated stent comprises a trunk region and at least one branch. The trunk region has a balloon expandable section and a self-expandable section. The balloon expandable section is less compressible than the self-expandable section. The branch is self-expandable and extends from the self-expandable section of the trunk region. The balloon expandable section is less compressible than the branch.

12 Claims, 3 Drawing Sheets

U.S. PATENT DOCUMENTS

| | | | |
|---|---|---|---|
| 6,520,988 B1 | 2/2003 | Colombo | 623/1 |
| 7,131,991 B2 * | 11/2006 | Zarins et al. | 623/1.13 |
| 2002/0019665 A1 * | 2/2002 | Dehdashtian et al. | 623/1.35 |
| 2003/0033002 A1 * | 2/2003 | Dehdashtian et al. | 623/1.13 |
| 2003/0114923 A1 * | 6/2003 | Swanick et al. | 623/1.35 |
| 2003/0195609 A1 | 10/2003 | Bernstein et al. | 623/1.15 |

FOREIGN PATENT DOCUMENTS

| | | |
|---|---|---|
| WO | 97/17912 | 5/1997 |
| WO | WO 97/17912 | 5/1997 |
| WO | 00/76423 | 12/2000 |
| WO | WO 00/76423 | 12/2000 |
| WO | 01/35864 | 5/2001 |
| WO | 03/04960 | 6/2003 |
| WO | WO 03/049640 | 6/2003 |
| WO | 03086237 A1 | 10/2003 |

OTHER PUBLICATIONS

Communication pursuant to Article 94(3) EPC from related European Application No. 04 780 261.6-2320. May 13, 2009. 3 pgs.

An Information Disclosure Statement filed in the present U.S. Appl. No. 10/643,261 dated Nov. 18, 2003. 8 pgs.

A Non-Final Office Action in the present U.S. Appl. No. 10/643,261 dated Sep. 5, 2006. 12 pgs.

* cited by examiner

STENT WITH IMPROVED RESISTANCE TO MIGRATION

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates to a stent for use in body lumens. More specifically, the present invention relates to a stent that is sufficiently flexible to facilitate its deployment and conformance to a tortuous lumen, and sufficiently rigid to resist migration, once the stent is deployed.

2. Description of the Related Art

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, mechanically expandable or hybrid expandable.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy, nickel, titanium, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern.

Some examples of stents or stent components that may be braided are described in U.S. Pat. Nos. 5,061,275, 4,655,771, 6,146,403, 5,836,966, 642,308, as well as in U.S. application Ser. No. 10/063,315 to Eder et al., filed Apr. 10, 2002.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to expand to a predetermined diameter in the vessel.

Some stents have been developed specifically to address the problems that arise in the treatment of stenoses at or near the site of a bifurcation of a body lumen are known in the art. Further, single bifurcated stents and grafts have been developed in order to treat such conditions at the site of a branch of a body lumen. A bifurcated stent and/or graft typically is configured in a "pant" design which comprises a tubular body or trunk and two tubular legs, however other configurations are also known wherein the stent includes a plurality of separate and/or inter-connectable portions which may be delivered to various positions at or around the bifurcation using a single or multiple catheters.

Some examples of bifurcated stents are shown in U.S. Pat. Nos. 5,723,004; 4,994,071 and 5,755,735.

In some stents, the compressible and flexible properties that assist in stent delivery may also result in a stent that has a tendency to migrate from its originally deployed position. It is thus desirable to provide a stent configuration that resists migration following deployment, particularly where the site of the desired deployment is within or adjacent to a vessel bifurcation.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention is embodied in a variety of forms. For example in at least one embodiment of the invention a stent is provided that is adapted both to resist migration within a body lumen and to conform to a tortuous installation path or installed location. The stent includes a first section, typically self-expandable, of predetermined compressibility adapted to permit the section to conform to the shape of the body lumen through which it is transmitted or surrounding the section when deployed. The stent also includes a second section which is balloon-expandable and which is less compressible than the first section. The second section is adapted to firmly engage that part of the body lumen surrounding the second section when it is deployed, or to engage the inner surface of another stent with which it is mated or assembled upon deployment.

In some embodiments the stent is a bifurcated stent. The stent comprises a trunk region and at least one leg region or branch extending therefrom. In at least one embodiment the trunk defines an opening which defines a first flow path therethrough and one or more branches adjacent thereto, wherein each branch defines additional flow paths.

Where the stent is bifurcated, the trunk region of the stent includes a proximal section and a distal section, wherein the branch(es) extend from the distal section. This distal section of the trunk region, as well as at least a portion of each branch, is constructed from braided strands of material. In some embodiments this braided portion of the stent is self-expandable. The proximal section of the trunk region comprises a solid, tubular geometry with cellular openings to provide a rigid construction within a section of the trunk region of the stent to assist in resisting migration of the stent-graft. In some embodiments the proximal section of the trunk region is balloon expandable.

In at least one embodiment, a modular mating stent is provided that is adapted to resist migration within a receiving stent. The modular mating stent includes a substantially self-expandable first section of predetermined compressibility adapted to permit the section to conform to the shape of a body lumen surrounding the section. The modular mating stent further includes a balloon-expandable second section less compressible than the first section adapted to firmly engage that part, i.e. the inner surface, of the receiving stent surrounding the second section when the two are assembled in a male-female relationship.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
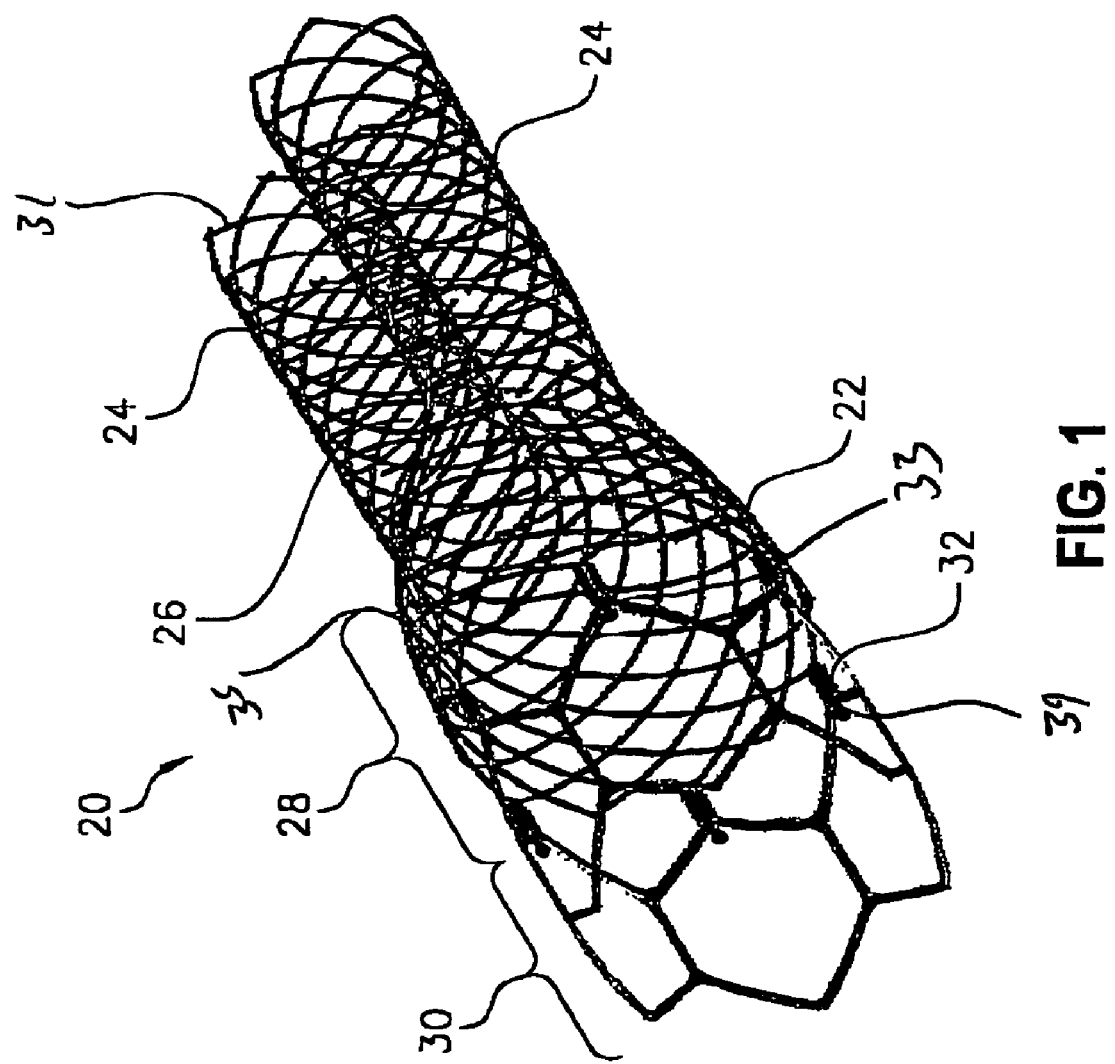
FIG. 1 is a perspective view of an embodiment of the invention comprising a bifurcated stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In at least one embodiment of the invention, such as for example the embodiment depicted in FIG. 1, there is shown a bifurcated stent 20 adapted to resist migration within a body lumen. Stent 20 includes a trunk region 22 at least one leg region or branches, such as branches 26 and 24, extending therefrom.

The trunk region 22 of stent 20 includes a first or proximal section 30 and a second or distal section 28. The branches 24 and 26 define separate flow paths which branch from the single flow path defined by the trunk region 22.

At least a portion of each branch 24 and 26, as well as the distal section 28 of the trunk region 22, share a common predetermined compressibility (or flexibility) adapted to permit the branches 24 and 26 and section 28 to conform to the shape of the body lumens surrounding them at their deployment site and to easily advanced through the tortuous confines of body lumen(s). In at least one embodiment the branches 24 and 26 as well as the section 28 are substantially self-expandable.

The proximal section 30 of the trunk region 22 is adapted to firmly engage that part of the body lumen surrounding the section 30 at its deployment site adjacent to the bifurcation of a vessel. The section 30 is deployed by mechanical or balloon expansion and is firmly seated within the vessel to resist stent migration. The section 30 likewise has a predetermined compressibility, but which is less compressible than that of the distal section 28 or the branches 24 and 26. In some embodiments section 30 is constructed from material having a substantially solid, tubular geometry with cellular openings, which may be obtained from a laser cut tube or sheet which formed into a tube.

In some embodiments, the distal section 28 and the branches 24 and 26 are integrally formed of one or more strands 31 of material that are interwoven or braided to form the respective portions of the stent 20.

The sections 28 and 30 may be bonded, welded, or otherwise engaged together to form the trunk region 22. In at least one embodiment, one or more distal members 33 of the proximal section 30 and one or more proximal members 35 of the distal section 28 are engaged together by at least one crimping members 32 (better seen in FIG. 2). A crimping member 32 comprises a tubular member or band 37 that is disposed about an overlapping portion of one or more distal members 33 and one or more proximal members 35. Once properly disposed, the crimping member is crimped or otherwise compressed in order to frictionally engage and retain the respective portions of members 33 and 35 contained therein.

In at least one embodiment, during delivery of the stent 20, when stent 20 is positioned at the correct location, distal section 28 of the trunk 22 and branches 24 and 26 are caused or allowed to self-expand to a predetermined diameter within the vessel(s). Even after the branches 24 and 26 and/or the section 28 are fully expanded, the location of stent 20 may be adjusted before final placement and fixation. Once properly positioned, the proximal section 30 of the trunk 22 is expanded to a predetermined diameter in the vessel via a balloon or other mechanical expansion mechanism such as are known.

Because of the greater rigidity of the proximal section 30, one the proximal section of the trunk 22 is fully expanded the stent 20 will remain fixed in its final position.

As indicated above, when the proximal section 30 is expanded, it is less compressible than the distal section 28 and delivers a substantial radial resistance to force, preventing stent 20 from working its way away from its originally deployed position.

In the embodiment shown in FIG. 1 the distal section 28 and branches 24 and 26 are formed of a conventional material to provide the section 28 and branches 24 and 26 with self-expanding characteristics. Suitable materials include, but are not limited to one or more shape-memory metals such as nitinol, one or more shape memory polymers, etc. The proximal section 30 is typically formed of any of a variety of materials that provide or can be made to provide greater rigidity or compression resistance than that of the distal section 28. Such materials may include but are not limited to stainless steel, nitinol, etc.

During balloon expansion of the proximal section 30, the material or materials of which the section 30 is constructed undergoes plastic deformation to better set the shape induced by the balloon expansion. The tendency of the more rigid section 30, to resist migration may be further enhanced by the inclusion of one or more vessel engagement members 39, a vessel engagement member may be comprised of one or more hooks, barbs, T-fasteners, and/or other external surface features to assist in firmly engaging the surrounding body lumen.

As stated above, the stent 20 may be a stent-graft, wherein the stent 20 is provided with a graft lining or covering to provide fluid pathways from the unbifurcated end to the bifurcated end.

As mentioned above, an alternative to the balloon-expandable stainless steel proximal section 30 is a balloon-expandable, and thus more rigid, proximal section 30 constructed of nitinol but annealed (i.e., heat treated above the temperature necessary to effect shape-memory retention). Annealing the nitinol transforms its material properties from a shape memory alloy capable of re-expansion to a more rigid structure, conducive to fixation through alternative means such as balloon expansion.

Figure 2:
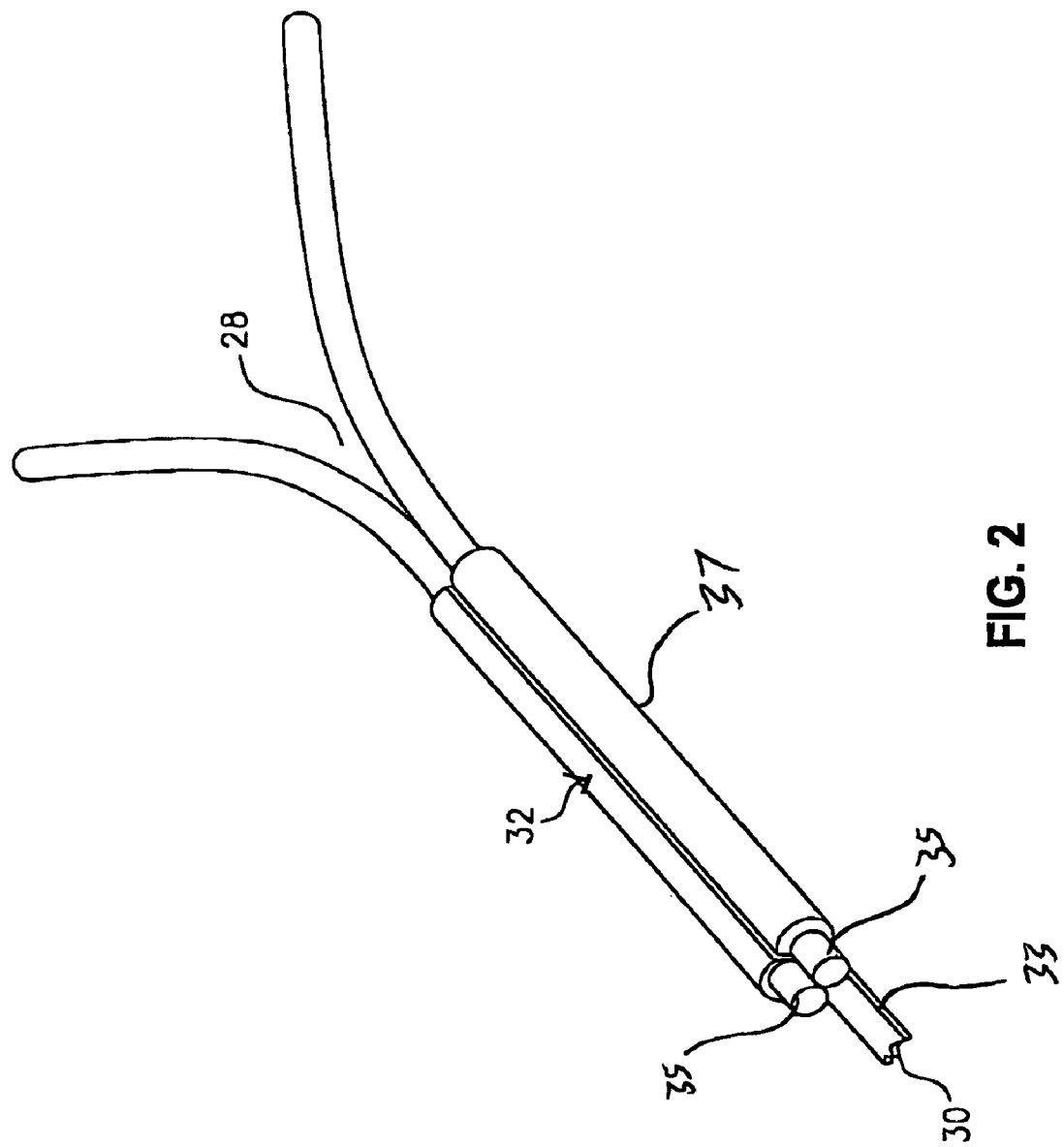
FIG. 2 is a perspective view of an embodiment of the invention comprising a crimping member that engages the two sections of differential compressibility in the trunk region of the stent of FIG. 1.

FIG. 2 is a detail view of crimping member 32 represented in FIG. 1 that secures the two sections of differential compressibility (i.e. section 28 and section 30) together. The exemplary configuration illustrates two braided members 35 of distal section 28 secured to one or more members 33 of the proximal section 30 via crimping member 32. In some embodiments crimping member 32 and/or other portions of the stent may be at least partially constructed of one or more radiopaque materials.

As indicated above, stent 20 is not limited to the use of crimping members 32 as a securing mechanism between the first and second sections 30 and 38 of the trunk region 22. For example, first section 30 and second section 28 may be secured together via welds, chemical or adhesive bonds, direct mechanical engagement (i.e. hooks, etc.) of the members 33 and 35, and any combinations thereof. Furthermore, the proximal section 30 and distal section 28 may not be connected at all if their relative positions are maintained in some other way, such as by securing section 28 and section 30 each to the inside of a graft, sleeve or other device via sutures or other securement mechanisms such as sutures.

Figure 3:
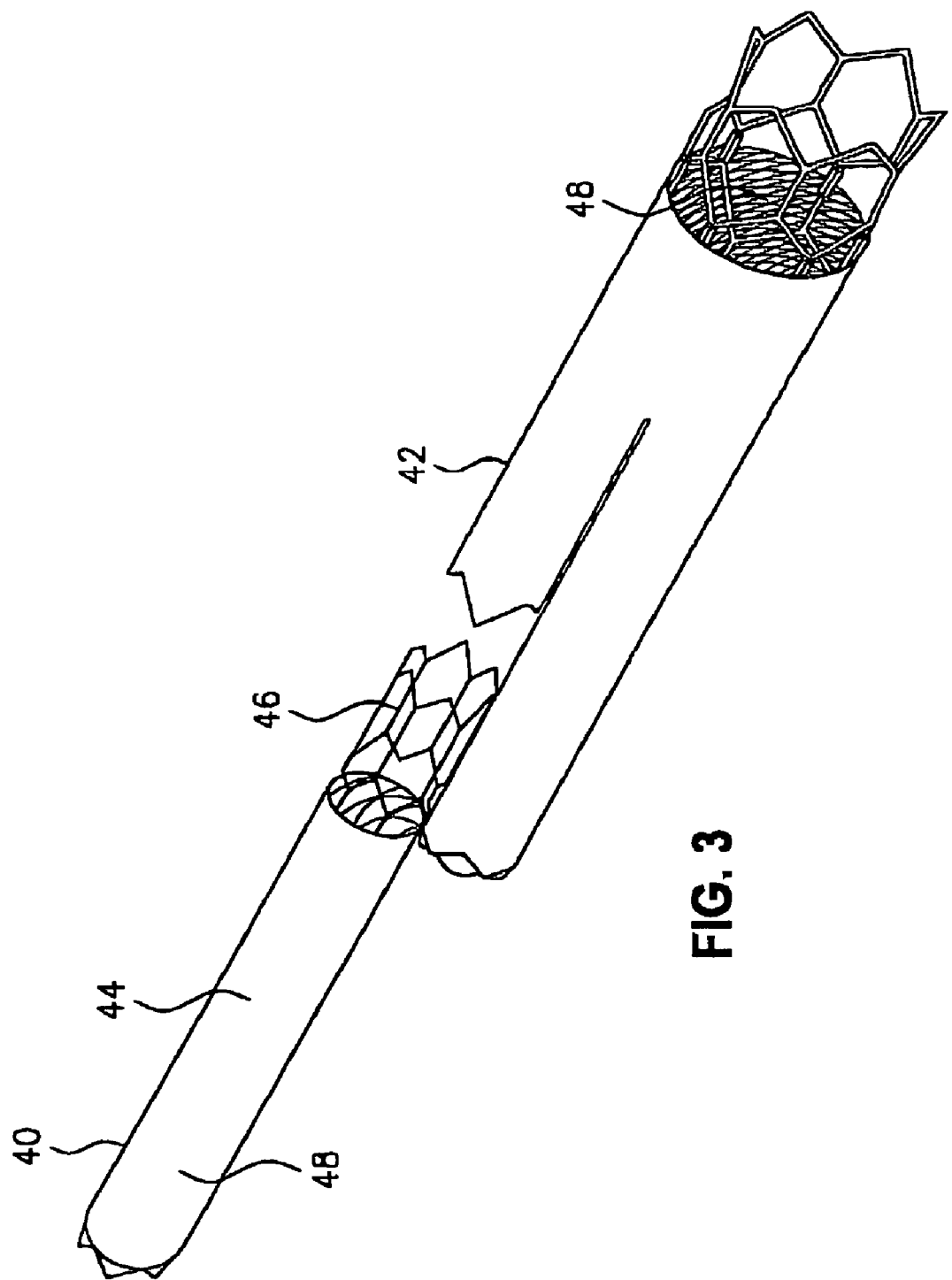
FIG. 3 is a perspective view of an embodiment of the invention comprising a modular mating stent adapted to be received within and assembled with a receiving stent in accordance with another embodiment of the present invention.

In at least on embodiment, the invention is also directed to a system comprising a modular mating stent 40 and receiving stent 42, an example of which is shown in FIG. 3.

The modular mating stent 40 includes a first section 44 of predetermined compressibility adapted to permit section 44 to conform to the shape of a body lumen surrounding section 44. The modular mating stent 40 further includes a second section 46 less compressible than first section 44 and adapted to firmly engage that part of receiving stent 42 surrounding second section 46, i.e. the inner surface of stent 42 in the area where stent 40 is received during in vivo deployment and assembly. A graft 48 covers modular mating stent 40 and receiving stent 42, at least in part, defining a fluid passageway.

The configuration and deployment of this embodiment of the present invention are essentially the same as those of the balloon-expandable embodiment of stent 20 described previously with reference to FIG. 1. First section 44 is constructed from braided strands of a shape memory alloy capable of re-expansion, while second section 46 is constructed from a non-shape memory alloy in a tubular geometry with cellular openings. Therefore, placement and fixation are achieved through alternative means such as balloon expansion. A notable difference from stent 20, however, is that mating stent 40 is deployed at least partially within receiving stent 42 as opposed to a body lumen, as represented in FIG. 3. The previously described principles of section 30 of stent 20 firmly engaging the surrounding body lumen apply to second section 46 of modular mating stent 40 firmly engaging the surrounding receiving stent 42 to resist migration and leakage.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A bifurcated stent being expandable from an unexpanded state to an expanded state, the stent comprising:
   a trunk region, the trunk region having a self-expandable section constructed from a first material and a balloon expandable section constructed from a second material, the balloon expandable section extending from a first end of the self-expandable section, in the expanded state the balloon expandable section is less compressible than the self-expandable section; and
   at least one self-expandable branch fixedly connected to and extending from a second end of the self-expandable section of the trunk region, in the expanded state the balloon expandable section is less compressible than the at least one self-expandable branch, wherein the self-expandable branch does not include a balloon-expandable section.

2. The stent of claim 1 wherein the balloon expandable section of the trunk region comprises a cut tube of stent material comprising a plurality of interconnected members defining a plurality of cell spaces.

3. The stent of claim 1 wherein the balloon expandable section of the trunk region comprises a cut sheet of stent material formed into a tubular shape, the tubular shape comprised of a plurality of interconnected members defining a plurality of cell spaces.

4. The stent of claim 1 wherein the self-expandable section of the trunk region and at least a portion of the at least one self-expandable branch is at least partially constructed from at least one strand of braided stent material.

5. The stent of claim 1 wherein the balloon expandable section of the trunk region comprises at least one distally extending member and the self-expandable section of the trunk region comprises at least one proximally extending member, the at least one proximally extending member and the at least one distally extending member being engaged to each other.

6. The stent of claim 5 further comprising at least one crimping member, the at least one crimping member disposed about the at least one proximally extending member and the at least one distally extending member.

7. The stent of claim 6 wherein the at least one crimping member is at least partially constructed of a radiopaque material.

8. The stent of claim 1 wherein the balloon expandable section of the trunk region is at least partially constructed of stainless steel.

9. The stent of claim 1 wherein at least one of the self-expandable section of the trunk region and the at least one self-expandable branch is at least partially constructed of a shape memory material.

10. The stent of claim 1 wherein the shape memory material is nitinol.

11. The stent of claim 1 further comprising at least one vessel engagement member, the at least one vessel engagement member extending from at least a portion of the balloon expandable section, the at least one vessel engagement member selected from the group consisting of hooks, barbs, T-fasteners, bumps, ridges, and any combination thereof.

12. The stent of claim 1 further comprising at least one layer of graft material, the at least one layer of graft material positioned on at least one of an inside surface and outside surface of at least a portion of at least one of the trunk region and the at least one self-expandable branch to define a fluid passageway therethrough.

* * * * *

UNITED STATES PATENT AND TRADEMARK OFFICE
CERTIFICATE OF CORRECTION

PATENT NO. : 7,628,806 B2
APPLICATION NO. : 10/643261
DATED : December 8, 2009
INVENTOR(S) : Yampolsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this

Second Day of November, 2010

David J. Kappos
*Director of the United States Patent and Trademark Office*